| 252-95 | AU 165 | EX |
| 7/13/76 | XR 3,969,387 | |

United States Patent [19]
Merkl

[11] 3,969,387

[45] July 13, 1976

[54] METALIC-ORGANO-PEROXIDE AND ORGANO-METALIC-PEROXIDE AND PREPARATION THEREOF

[76] Inventor: George G. Merkl, 46 Sunset Court, Haworth, N.J. 07641

[22] Filed: Dec. 29, 1972

[21] Appl. No.: 319,293

[52] U.S. Cl. .................. 260/448 R; 252/431 C; 252/95; 260/212; 260/233; 260/3 R; 260/414
[51] Int. Cl.$^2$ ............................................. C07F 5/06
[58] Field of Search ......... 260/448 AD, 448 R, 448, 260/414

[56] References Cited
UNITED STATES PATENTS

| 1,068,777 | 7/1913 | Jonas et al. | 260/448 R |
| 1,079,916 | 11/1913 | Jonas et al. | 260/448 R |
| 1,793,935 | 2/1931 | Kaufler et al. | 260/448 AD |
| 1,870,859 | 8/1932 | Maximoff | 260/448 R |
| 2,141,477 | 12/1938 | Losch | 260/448 R |

FOREIGN PATENTS OR APPLICATIONS

| 348,790 | 5/1931 | United Kingdom | 260/448 R |

OTHER PUBLICATIONS
Chemical Abstracts, vol. 57, 3464i (1962).
Chemical Abstracts, vol. 57, 12698g (1962).
Chemical Abstracts, vol. 61, 4485g (1964).
Chemical Abstracts, vol. 72, 127968p (1970).

*Primary Examiner*—H. Sneed
*Attorney, Agent, or Firm*—Arnold, White & Durkee

[57] ABSTRACT

Peroxide compounds are prepared by contacting and reacting a reactive aluminum, i.e., highly pure aluminum permeated with a metal having an atomic volume close to hydrogen, e.g., mercury, indium or gallium, with the combination of hydrogen peroxide and a carboxylic acid. These compounds are useful in detergents and as catalysts.

31 Claims, 4 Drawing Figures

ALUMINUM ADIPIC PEROXIDE

FIG. 3

ALUMINUM PHTHALIC PEROXIDE

FIG. 4

ALUMINUM ACRYLIC PEROXIDE

METALIC-ORGANO-PEROXIDE AND ORGANO-METALIC-PEROXIDE AND PREPARATION THEREOF

CROSS-REFERENCE TO RELATED APPLICATIONS

Reference is made to the following copending patent applications: Catalytic Electrode, Ser. No. 211,979, filed Dec. 27, 1971 now abandoned; Aluminum Salts of Carboxylic Acid, Ser. No. 255,757, filed May 22, 1972; and Polymeric Salts of Carboxylic Acid; and Resins, filed Nov. 13, 1972, Ser. No. 305,819.

BACKGROUND OF THE INVENTION

The present invention relates to a method for the formation of metallic-organo-peroxides and organo-metallic peroxides and to such compounds so produced.

Many methods for forming organo-peroxides are known. Reference is made to the book, "Hydrogen Peroxide in Organic Chemistry" by John G. Wallace, published by the Electro Chemical Department of E. I. du Pont De Nemours and Company.

Generally, an organic peroxide is defined as a derivative formed by replacing one or both hydrogen atoms of hydrogen peroxide by an organic radical. The present method produces compounds which include a metal atom bonded to an organic radical and a peroxide type group bonded to the organic radical. The peroxide group is of the oxygen to oxygen type bond in which a hydrogen atom can be connected to one of the oxygen atoms. The method of the present invention also produces a product wherein the organic radical has a metallic atom bonded to it and the peroxide group is bonded to the metal atom. The differences in the types of products produced gives rise to the distinction between the description of the product as being on the one hand, a metallic-organo-peroxide and on the other hand, an organo-metallic-peroxides.

One elementary method of producing an organic peroxide makes use of the fact that a strong aliphatic acid solution with hydrogen peroxide exists in equilibrium with the corresponding organic peracid.

However, in the absence of a strong acid catalyst, such as a mineral acid, the attainment of equilibrium is impractically slow, especially at temperatures below 40°C. At higher temperatures, it is difficult to prevent the excessive loss of active oxygen unless the oxidizable organic substance is also present to react with the organic peracid as it forms. For this reason, it is common practice, whenever possible, to employ hydrogen peroxide under conditions for the in situ formation of the organic peracid at temperatures ranging up to the boiling point of the aliphatic acid.

The peracid formed in situ can be reacted with an olefinic material to produce an epoxy (oxirane) compound as a primary product.

The reaction, is, of course, two-staged, since the peracid must be formed first.

Common organic peracid systems include glacial acetic acid or formic acid with hydrogen peroxide. The organic peracids thus formed are unstable and considered a hazard particularly when the organic peracid is relatively concentrated.

It is known that the mild oxidizing action of hydrogen peroxide is increased considerably by use of certain metallic catalysts. One example of a metallic catalyst is ferrous sulfate which is employed in a redox system:

it has been employed with hydrogen peroxide and is generally known as Fenton's Reagent. Other catalysts include osmium and tungstic oxides employed to hydroxylate aromatic and unsaturated hydrocarbons and to effect other oxidations. These additional catalysts are classed as Milas' Reagents which together with Fenton's Reagent constitute the bulk of the metal activated hydrogen peroxide systems. Hydrogen peroxide in metal-activated systems reacts as though it was dissociating into two hydroxyl radicals.

Fenton's oxidations are, in fact, believed to proceed through the intermediate formation of hydroxyl free radicals:

The $Fe^{++}$—$F^{+++}$ system, and such other redox systems as $Cu^+ - Cu^{++}$, are normally employed with hydrogen peroxide in aqueous acid medium. A small amount of sulfuric acid is added to an aqueous solution of ferrous sulfate heptahydrate so that Fenton's oxidations are carried out at a pH of. 1–4. In a less acid solution, the reaction efficiency is decreased, and hydrogen peroxide is catalytically decomposed.

Other metal-activated systems include in decreasing order of catalytic efficiency the following:

Derivatives of the aforementioned catalyst, such as phosphotungstic acids (e.g. $H_3PO_4 12WO_3$) are also effective as catalysts for hydrogen peroxide.

The prior art shows four general methods of incorporating the peroxide bond (—OO—) into organic molecules. These methods include auto-oxidation, ozonization, the association of oxygenated free radicals, and the addition and substitution reactions of hydrogen peroxide and hydroperoxides. Typically, hydrogen peroxide is related with acids, anhydrides, esters, alcohols, organic sulfates and sulfonates, carbonyl compounds, and organic chlorine compounds to produce organic peroxides.

The reactions of acids anhydrides and esters with hydrogen peroxide ordinarily lead to the formation of organic peracids, although other organic percompounds may result. The most popular method of preparing a peracid is by mixing hydrogen peroxide and an aliphatic acid in the presence of a strong acid catalyst such as sulfuric acid. Typically an equimolar mixture of high strength hydrogen peroxide and acetic acid with one percent sulfuric acid catalyst reaches equilibrium after standing for 12 to 16 hours.

The resin technique for peracetic acid formation is considered much faster and permits continuous or batchwise preparation.

The resin technique or peracetic acid formation is operated simply by passing a mixture of glacial acetic acid and hydrogen peroxide through a cation exchange resin column. The column contains polystyrene sulfonic acid resin which has been treated with glacial acetic acid to remove excess water. Under conditions for operation of the resin technique, a contact time of 12 to 16 minutes at about 45°C is sufficient for maximum conversion of hydrogen peroxide to peracetic acid. The serious drawback in this method is that it requires high strength hydrogen peroxide and thus creates a serious hazard.

A common procedure for converting an alcohol, R-O-H, to a hydroperoxide, R-OOH, consists of reacting hydrogen peroxide and tertiary alcohols in strong sulfuric acid. The reaction is believed to involve the formation of an intermediate sulfate and, therefore, is similar to the alkylation of hydrogen peroxide by dialkyl sulfates. The reaction often results in serious explosions, although the final products of such reactions are relatively stable. Prior art methods do not produce peroxide products with primary or secondary alcohols very easily. Mixtures of a tertiary alcohol and hydrogen peroxide have been used as germicides, fungicides, bleaching agents, and peroxide reagents.

The strong sulfuric acid used in the hydrogen peroxide - alcohol reaction is sometimes replaced by heteropolyacids having multiple inorganic acid radicals. The heteropolyacids which are soluble in ether, contain the elements of phosphorus, silicon, or boron, coordinated with a metallic oxide such as tungsten oxide. The characteristic solubility of heteropolyacids allows the preparation of alkyl hydroperoxides to be carried out in ether.

The known methods of converting carbinols of many types to hydroperoxides and disubstituted peroxides makes use of strong sulfuric acid as a catalyst. Typically, acetylene peroxides are formed by the interaction of hydrogen peroxide and the hydroxyl group of acetylenic carbinols in the presence of strong sulfuric acid. The peroxides thus formed are unusually stable despite the presence of the acetylenic bond.

Dialkyl sulfates and alkyl hydrogen sulfates can be used to produce hydroperoxides and dialkyl peroxides by a reaction with alkaline hydrogen peroxide. These peroxides are often used as polymerization catalysts and diesel fuel additives. Typically, primary and secondary dialkyl peroxides are prepared by the alkylation of hydrogen peroxide with alkyl methane sulfonates in liquid alkaline methanolic solution. A known method for producing sodium peroxy sulfonates is carried out by reacting a sulfonic acid such as naphthalene sulfonic acid and sodium peroxide in a liquid medium. The operation is conducted in a cold environment to reduce the violence of the reaction. The peroxy product obtained has approximately 6% active oxygen and is considered useful as a bleaching agent or insecticide.

Olefins have been transformed to hydroperoxides in a reaction which amounts to the addition of hydrogen peroxide to the double bond. The reaction, however, is conducted in strong sulfuric acid according to known methods and probably involves the formation of an intermediate sulfate.

The preparation typically takes place at below 0°C and takes several hours.

It is known that hydrogen peroxide can be reacted with an aldehyde or a ketone in the presence of a catalyst to form a peroxide compound. The following equilibrium is believed to occur for an aldehyde and hydrogen peroxide:

Typically, formaldehyde is treated with hydrogen peroxide in ether in the presence of $P_2O_5$. The peroxide product is very explosive. Both cyclic ketones and aliphatic ketones have a tendency to form stable but hazardous peroxides. As a rule, known methods produce unstable peroxides of aromatic ketones and aromatic aldehydes because of the greater ease of migration of the phenyl radicals attached to the carbonyl carbon.

It is known that organic peroxides can be formed by reacting hydrogen peroxide with organic chlorine compounds. The reaction is generally conducted in the presence of a chlorine acceptor which may be caustic or organic bases such as pyridine.

SUMMARY OF THE INVENTION

One of the principal objects of the invention is to provide a peroxide compound comprising the steps of preparing a reactive aluminum and reacting the reactive aluminum with a liquid mixture of hydrogen peroxide and an organic compound. Another object of the present invention is to provide a method for forming a metallic-organo-peroxide comprising the steps of forming a reactive aluminum and contacting a liquid mixture of hydrogen peroxide and an organic compound with the reactive aluminum. Another object of the invention is to provide a method for forming an organometallic-peroxide comprising the steps of forming a reactive aluminum and contacting a liquid mixture of hydrogen peroxide and an organic compound with the reactive aluminum.

Another object of the invention is to provide a method of forming a percarboxylic acid comprising the steps of forming a reactive aluminum and contacting a liquid mixture of a carboxylic acid and hydrogen peroxide with the reactive aluminum.

The invention accordingly comprises the several steps and the relation of one or more of such steps with respect to each of the others, or as exemplified in the following detailed disclosure, and the scope of the application of which will be indicated in the claims.

BRIEF DESCRIPTION OF THE DRAWINGS

For a fuller understanding of the nature and object of the invention, reference should be had to the following detailed description, taken in connection with the accompanying drawings, in which.

THE INVENTION

The present invention is focused on the utilization of the catalytic properties of a reactive aluminum prepared by the methods described in co-pending patent application, "Catalytic Electrode," Ser. No. 211,979 filed Dec. 27, 1971, now abandoned.

The reactive aluminum in the present disclosure corresponds to the aluminum catalytic electrode described in the aforementioned patent application.

Generally, a reactive aluminum is prepared by contacting highly pure aluminum in the presence of a hydrogen ion source with a metal which can form a hydride. The hydrogen ion source can be an inorganic acid or the like or an inorganic acid such as citric acid or acetic acid or the like. The reactive aluminum in an alkali solution such as water and sodium hydroxide will serve as a hydrogen ion source for the formation of another reactive aluminum.

The metal for forming the reactive aluminum can be an element or an alloy. Preferably, the metal is gallium, or indium or an alloy of the two or mercury. A desirable characteristic of the metal is that it is soft and pliable and preferably a liquid during the process in order to permit the rapid permeation through the aluminum. The general rule is that an element with an atomic volume near that of hydrogen is preferred for this metal.

It should be understood that the term "highly pure" herein means greater than 99% and that purities in the order of 99.9% and 99.99% are preferable.

One simple method of preparing a reactive aluminum is to use an aluminum piece, such as a rod 99.99% pure having a length of three inches and a diameter of a half inch. The aluminum rod is placed on its side in a glass dish and sufficient 2N acid, such as hydrochloric acid, is added to cover the aluminum rod. The aluminum rod is contacted with the metal such as mercury or gallium and the metal is given time to permeate the aluminum rod. Of course, the aluminum rod can be treated in a vertical position if desired and a rod shape is not necessary. Other shapes may be used.

The concentration of the acid can cover the broadest range to even include neutral water. The choice of the hydrogen ion source such as an acid will depend upon the peroxide compound to be formed and the concern over impurities.

It is preferable to prepare the aluminum rod for the reaction by at least partially stripping the aluminum oxide coating which has formed on the surface due to the exposure to air and moisture. If the aluminum rod has been stripped, then hot water can serve as the hydrogen ion source. Otherwise, it may be desirable to start out with an acid to strip off the oxide coating on the aluminum rod in order to initiate the reaction to form the reactive aluminum as quickly as possible. Of course, the aluminum rod may be stripped mechanically with sandpaper or a file or the like.

The inter-reaction which occurs between the aluminum rod and the acid, gives rise at the start to the formation of large bubbles which rise up to the surface through the acid. After a while it will be observed that instead of large bubbles forming at the top of the aluminum rod and then breaking free and rising to the surface of the acid, tiny bubbles will be eminating from may parts of the upper surface of the aluminum rod. The occurrence of the multitude of tiny bubbles indicates that the aluminum rod is being coverted into a "reactive" aluminum.

Generally, the aluminum rod will take up or absorb from 0.1 to 5 percent of the mercury by weight depending upon how long the reaction is permitted to continue. A range of 2 to 3 percent of the mercury by weight is desired for many applications. However, in some applications as little as 0.1 percent of the mercury by weight is preferred.

The reaction can be stopped on the basis of the increased weight of the auminum rod due to the absorption of the metal or due to the production of a multitude of tiny bubbles for a period of ten to fifteen minutes or due to the observance of the hydrolysis of water when the aluminum rod being treated is placed therein.

An aluminum rod treated as described, displays surprisingly active catalytic properties not at all suggested by the prior art. The prior art has recognized that aluminum and an amalgam of aluminum exhibit catalytic properties. It is of considerable significance that the treatment of highly pure aluminum as described herein exhibits catalytic and initiating properties that far exceed prior art contemplation.

Another method of preparing a reactive aluminum uses gallium instead of mercury. The same aluminum rod is placed in a glass dish and covered with hydrochloric acid and one end of the aluminum rod is contacted with the gallium having a mass of from one to three percent of the aluminum rod. The treatment takes from ten to fifteen minutes depending upon how well the oxide coating on the aluminum rod has been removed at the point of contact of the gallium and the aluminum rod. A fairly clean part of the aluminum rod is indicated by the observance of large bubbles generated thereat.

It is desirable to dip a reactive aluminum formed with gallium into anhydrous alcohol immediately after completion of the process in order to prevent the formation of a brownish compound on the aluminum rod thereafter.

The amount of the metal in the aluminum rod can be varied in accordance with applications. In general, if a high percent of the metal by weight is desired, quick cooling of the reactive aluminum rod after formation will prevent the squeezing out of the metal due to an exothermic reaction. Water is convenient for this purpose for a reactive aluminum formed with mercury. However, in cases where it is desired to reduce the amount of, say, mercury from several percent by weight to, say, 0.1% by weight, the reactive aluminum can be heated to squeeze out the mercury.

From the above, it is clear herein, including the claims, what is meant by a "reactive aluminum".

The reactive aluminum exhibits an aligned matrix and, it is believed, capable of converting at least partially to a hydride at one or more valences and produces $Al^{+++}$, $e^-$, $H^+$, $OH^-$, $HO_2^{--}$, and $O^{--}$ radicals depending upon the fluid contacting the reactive aluminum. Where the fluid is hydrogen peroxide, it is believed that $O_2^-$ and $O_2^{--}$ radicals are produced in addition to the aforementioned radicals.

Certain impurities such as copper and iron, inhibit the formation of a reactive aluminum and so should be avoided in the aluminum rod. Impurities which inhibit or promote the reaction are given in the aforementioned catalytic electrode application.

It is an important aspect of the present invention the realization that the aforementioned treatment of highly pure aluminum results in a reactive aluminum which can bring about a reaction with an organic compound and hydrogen perodixe to form a peroxide compound. The reactive aluminum not only brings about the formation of the peroxide compound, but further results in the aluminum from the reactive aluminum entering into the peroxide compound to form a part thereof. The amount of aluminum which forms a part of the peroxide compound can vary from a fraction of a percent to five percent or more.

Generally, the reaction time for the production for most of the peroxides in accordance with the present invention is considerably shorter than the time taken by prior art methods. The rate of the reaction for the production of a peroxide in accordance with the present methods will be determined by well known parameters, such as the concentration of the hydrogen peroxide, the temperature of the constitutents, the quantity of the reactive aluminum, and other factors.

If a reaction is permitted to proceed too rapidly so that the exothermic reaction elevates the temperature of the constituents, there is a possibility that the hydrogen peroxide will tend to break up into water and oxygen and thereby reduce the concentration of the hydrogen peroxide. Hence, there will be fewer peroxide groups available for the formation of the desired peroxide compound.

One approach for controlling the reaction rate is to add the hydrogen peroxide a little at a time. Of course, this presumes the presence of a liquid organic compound already present in order to form the mixture with the hydrogen peroxide.

Of course, a dilute hydrogen peroxide can be used in order to reduce the exothermic reaction to produce a relativey low-grade peroxide compound without the incidence of an elevated temperature or a reaction which requires some monitoring.

Generally, the atomic bonding in an organic peroxide formed by the present methods will be dependent upon the bonding that is present in the organic compound used in the reaction with hydrogen peroxide in the presence of the reactive aluminum. For example, it is well known that double bonds in organic compounds tend to be preferred sites for inter-reaction or reactions in general.

In the case where the organic compounds include other than single bonds such as double bonds, triple bonds, multiple bonds in general, or the like, an organic peroxide having a peroxide or hydroperoxide group attached directly to an oganic group can be produced. Since the organic peroxide product in this case also includes an aluminum atom, it is proper to describe such products as a metallic-organic-peroxide.

Typically, the formation of a metallic-organic-peroxide includes the step of reacting the selected organic compound with hydrogen peroxide in the presence of the reactive aluminum. Carboxylic acids are suitable organic compounds. The presence of a ring structure in the organic compounds does not affect the formation of an organic peroxide by the present methods.

It is interesting to note that in the article entitled, "Thermochemistry of the Hydrogen Polyoxides $H_2O_3$ and $H_2O_4$" by Paul A Giguere, published in the Transactions New York Academy of Sciences, that the presence of three radicals of $H_2O_3$ and $H_2O_4$ were prepared and measured under the extreme conditions of temperature of less than 100°K. Furthermore, this article indicates that the formation of higher order hydrogen polyoxides are extremely difficult and require extreme temperature and pressure requirements. Although no limitation is intended to be suggested by the presentation of theories related to the operation of the present invention, it is believed that in carrying out the present invention there is a considerable production of radicals of $H_2O_3^{--}$ and $H_2O_4^{--}$ due to the reactive aluminum reacting with the hydrogen peroxide. It has been observed that during the formation of an organic peroxide by the combination of carboxylic acid and concentrated hydrogen peroxide, the removal of the reactive aluminum from the mixture into air produced a red mecuric oxide on the reactive aluminum which had been prepared with mercury. The formation of red mecuric oxide rather than black mecuric oxide is an indication of $O_2^-$ radicals which points to the aforementioned polyoxide radicals. In another experiment, part of an organic peroxide prepared with a carboxylic acid, was contacted with some mercury and immediately produced red mecuric oxide which for the same reason given previously, tends to confirm the proposed theory. Also, it is known from the aforementioned article that O-O stretching for $H_2O_3$ occurs at 760 $cm^{-1}$ and corresponding absorption is clearly shown in the infrared spectra curves of FIGS. 2 to 4.

The production of higher order polyoxide radicals is favored by the use of highly concentrated hydrogen peroxide in the order of 50% and the use of elevated temperatures above 50°C. There is the possibility that the use of highly concentrated hydrogen peroxide at an elevated temperature may tend to cause a very quick breakdown of the hydrogen peroxide so that the reaction carried out at an elevated temperature will tend to readily reduce the concentration of the hydrogen peroxide. However, in one case it was determined that 300 grams of 50% hydrogen peroxide were reacted with 209 grams of adipic acid and the indications are that as much as 280 grams of the hydrogen peroxide were actively interacted with the adipic acid due to the presence of the reactive aluminum. In another case,

150 grams of 50% concentrated hydrogen peroxide were reacted with 72 grams of acrylic acid in the presence of a reactive aluminum and the product which resulted shows the presence of peroxide type groups, both at the previous carbon to carbon double bond and carbon to oxygen double bonds.

An interesting theory has been evolved to explain the formation of organic peroxides in terms of the present methods. The theory is not intended to be a limitation. To start with, in a typical reaction involving hydrogen peroxide with a carboxylic acid, the carboxylic acid which is represented as RCOOH forms a layer around the reactive aluminum rod and the hydrogen peroxide forms a layer on the layer of the carboxylic acid. A layer of the carboxylic acid then forms about the hydrogen peroxide layer and it continues alternating between the two types of layers. This can be shown diagrammatically by the following:

TABLE 1

| R C O O | H |   | R C O | O | H |   | R C | O O |   | H |   |
|---------|---|---|-------|---|---|---|-----|-----|---|---|---|
| O H | H | O |   | O | H | H O |   | O H | H O |   |   |
|   | R C O | O | H |   | R C | O O |   | H |   | R C | O O | H |
|   | O | H | O |   |   | O H |   | H O |   |   | O H | H O |
|   |   | R | C | O O |   | H |   | R | C O O |   | H |   | R C | O O | H |
|   |   |   |   | O H |   | H | O |   | O H |   | H O |   |   | O H | H O |

In accordance with the hypothesis given herein, Table 1 shows the arrangement of the layers of carboxylic acid and hydrogen peroxide alternating and having an atomic arrangement corresponding with the charges of the atoms present therein. The cells shown in Table 1 indicate the cooperation between atoms to produce radicals which will eventually combine with aluminum atoms to form the metallic-organo-peroxide. It is seen that the radical RCOOH is formed while hydrogen atoms which break away from the carboxylic acid atoms combine with hydroxyl atoms from the hydrogen peroxide to produce water. The hydrogen atoms readily diffuse about and through the matrix of the reactive aluminum to interact therein and ultimately the formation of the aluminum carboxylic peroxide takes the form of It is believed that the unusual stability of the organic peroxides prepared in accordance with the present methods is due to the fact that if the oxygen atom between the carbon and aluminum atoms is dislodged, the aluminum atom will immediately couple over to the carbon atom to restore the stability of the atomic structure. In the proposed form, it is noted that the aluminum atom acts as a cross-link between the organic peroxide groups.

Highly concentrated hydrogen peroxide has a tendency to produce hydroperoxy groups which are relatively stable radicals as compared to other peroxide type radicals. The hypothesis for the interreaction between a carboxylic acid and a weak hydrogen peroxide solution equals a somewhat similar hypothesis as given above in that alternate layers are produced on the reactive aluminum but the pattern is as shown in

TABLE 2

| R C O O | H |   | R C O O |   | H | R C | O |   | O | H |   |
|---------|---|---|---------|---|---|-----|---|---|---|---|---|
| H O | O |   | H O |   | O |   | H | O O |   | O |   |
|   | R C O | O H | R C |   | O O | H |   | R | C |   | O | O H |
|   | H | O O |   |   | H O O |   |   |   | H |   | O O |
|   |   | R | C O O | H |   | R C O |   | O |   | H |   | R | C O | O H |
|   |   |   | H O O |   |   | H | O |   | O |   |   | H | O O |

As can be seen, the layers of the carboxylic acid alternate with hydroperoxy radicals. The organization of the atoms with respect to each other is based on the supposed interreaction between the charges carried by the various radicals. The cells indicated in Table 2 suggest how the various atoms and radicals interreact in order to bring about the formation of the aluminum carboxylic peroxide. The presence of the hydroperoxide groups tends to give rise to hydroxyl atoms as the desired product is being formed. It is believed that the hydrogen radicals diffuse into the reactive aluminum. It may be that the overall reaction which occurs for hydrogen peroxide and a carboxylic acid is some combination of the illustrated reaction formats given in Tables 1 and 2. Furthermore, it may be that the resulting organic peroxide contains hydroperoxide groups.

FIGS. 1 to 4 show the infrared spectra of four of the organic peroxides prepared in accordance with the present methods. The samples for each of the curves were prepared in a dry form which were mixed with potassium bromide to form a disk in accordance with the standard techniques. The scan speed for the aluminum acrylic peroxide, aluminum phthalic peroxide, and aluminum acetic peroxide was medium, whereas the scan speed for the aluminum adipic peroxide was fast. The analysis or interpretation of infrared spectra is a difficult and expanding art but some comments can be made with respect to FIGS. 1 to 4, although no limitation is intended. Broadly, it is known that absorption in the region of 3400 $m^{-1}$ can be attributed to the presence of hydroxyl groups and peroxy groups. The wide absorption band tends to show that the organic peroxide has an abundance of peroxy groups. Of course, the aluminum adipic peroxide does not show the same broad absorption about 3400 $m^{-1}$ but this can be attributed to the fact that the adipic acid contains a carbon to carbon double bond and two carboxylic groups so that in the complexity of the reaction the bonding of the peroxy groups does not readily show up in the infrared spectra. A separate test run on the aluminum adipic peroxide showed 10% free $O^-$ which can be taken to correspond to the successful introduction of 20% of the hydrogen peroxide into the susceptible double bonds at the carbon to carbon bonds and within the carboxylic groups of the adipic acid. However, the infrared spectra of the aluminum adipic peroxide used for the generation of FIG. 3 was not reacted to form a complete organic peroxide so that the presence of carboxylic groups appears, mainly at 1590 $cm^{-1}$ and 1560 $cm^{-1}$. It is believed that peroxyl groups are indicated by the absorptions at 1280 $cm^{-1}$, 1190 $cm^{-1}$, and 990 $cm^{-1}$. It is interesting to compare the aluminum acetic peroxide and aluminum acetohydrate shown in FIG. 4. The aluminum acetohydrate corresponds to the polymeric aluminum acetate prepared in accordance with patent application Ser. No. 255,757 filed May 22, 1972 for Metal Salts of Carboxylic Acids. Attention is drawn to the distinctive absorption bands of the aluminum acetic peroxide. The aluminum acetohydrate also shows the presence of peroxy groups; the occurrence of the absorption band in the vicinity of 3500 $cm^{-1}$.

It is of interest that any of the metal salts of carboxylic acid of the aforementioned patent application can be reacted with hydrogen peroxide in the presence of reactive aluminum to produce an organic peroxide.

It is of interest that generally hydrogen peroxide is the preferred reactant but the essential features of the production of organic peroxide rely only on the presence of $O^-$ radicals or the like. Known methods of producing the desired radicals include, for example, the use of ultraviolet light on a mixture containing water to produce $O_3^-$ radicals. Another way of getting the desired radicals is to generate ozone and bubble it through the mixture which will be used to produce the organic peroxide. Other equivalent means for providing the desired radicals will be obvious to those skilled in the art.

The use of hydrogen peroxide with the concentration of about 30% is convenient and the examples given herein were performed using hydrogen peroxide with a 30% concentration except where indicated differently. Also, most experiments carried out were done at a temperature below 50°C, but, of course, as it has been noted, it is sometimes desirable to use an elevated temperature in order to increase the occurrence of peroxide radicals. As noted previously, organic peroxides have many known uses. The present organic peroxides provide a novel use as a catalyst for the formation of resins since it is possible to use an organic peroxide of the same organic radical corresponding to the main organic radical in the resin. This is an attractive use since no problem of removing the catalyst occurs since the catalyst becomes an integral and tolerable component in the resin formed thereby.

EXAMPLES

Illustrative, non-limiting examples of the practice of the invention are set out below. Numerous other examples can readily be evolved in the light of the guiding principles and teachings contained herein. The examples are intended merely to illustrate the invention and not in any sense to limit the manner in which the invention can be practiced. The parts and percentages recited therein and all through this specification, unless specifically provided otherwise, refer to parts by weight and percentages by weight.

EXAMPLE 1

An aluminum terephthalic peroxide is formed by combining 121 grams of terephthalic acid with 50 grams of hydrogen peroxide in the presence of a reactive aluminum rod of about 54 grams. The hydrogen peroxide is added slowly to the terephthalic acid in order to maintain the reaction at a slow rate. The reaction may be permitted to continue in the presence of the reactive aluminum until the resulting product becomes highly viscous, then the reactive aluminum is removed so as not to permit the entrapment of mercury or the like which is used in the preparation of the reactive aluminum.

EXAMPLE 2

An aluminum formic peroxide is formed by using 90 grams of formic acid and otherwise repeating the process of Example 1.

EXAMPLE 3

An aluminum propionic peroxide is formed by using 74 grams of propionic acid and otherwise following the procedure of Example 1.

EXAMPLE 4

An aluminum palmitic peroxide is formed by using 256 grams of palmitic acid following the procedure of Example 1.

EXAMPLE 5

An aluminum myristic peroxide is formed by using 228 grams of myristic acid and otherwise following the procedure of Example 1.

EXAMPLE 6

An aluminum butyric peroxide is formed by using 88 grams of butyric acid and otherwise following the procedure of Example 1.

EXAMPLE 7

An aluminum acetic peroxide is formed by using 60 grams of acetic acid and otherwise following the procedure of Example 1.

EXAMPLE 8

An aluminum phthalic peroxide is formed by using 160 grams of phthalic acid and otherwise following the procedure of Example 1.

EXAMPLE 9

An aluminum caprylic peroxide is formed by using 144 grams of caprylic acid and otherwise following the procedure of Example 1.

EXAMPLE 10

An aluminum tartaric peroxide is formed by using 120 grams of tartaric acid and 100 grams of hydrogen peroxide but otherwise following the procedure of Example 1.

EXAMPLE 11

An aluminum ascorbic peroxide is formed by using 176 grams of ascorbic acid and 100 grams of hydrogen peroxide but otherwise following the procedure of Example 1.

EXAMPLE 12

An aluminum adipic peroxide is formed by combining 309 grams of hydrogen peroxide with 209 grams of adipic acid and reacting the mixture with a reactive aluminum rod of about 169 grams mass. The hydrogen peroxide should be added gradually and the reaction takes about ½ hour to complete.

EXAMPLE 13

An aluminum lauric peroxide complex is formed by reacting 200 grams of lauric acid, 40 grams of hydrogen peroxide, and 50 grams of ethyl alcohol with a 50 gram rod of a reactive aluminum.

EXAMPLE 14

An aluminum acetic peroxide is formed by first reacting 60 grams of acetic acid with 366 grams of water with 54 grams of a reactive aluminum rod to form a hydrate and then adding 40 grams of hydrogen peroxide until a pasty product forms and then decanting and drying the product.

EXAMPLE 15

An aluminum acrylic peroxide is formed by reacting 72 grams of acrylic acid with 37 grams of water for about 10 minutes with a reactive aluminum rod of about 54 grams and then adding 40 grams of hydrogen peroxide slowly. The reaction should be permitted to continue for about 10 minutes thereafter.

EXAMPLE 16

An aluminum citric peroxide is formed by first reacting 192 grams of citric acid with 499 grams of water with a reactive aluminum rod of 54 grams and then gradually adding 100 grams of hydrogen peroxide.

EXAMPLE 17

An aluminum gluconic peroxide is formed by first reacting 196 grams of gluconic acid with 307 grams of water with a reactive aluminum rod of about 54 grams and then adding 80 grams of hydrogan peroxide.

EXAMPLE 18

An aluminum maleic peroxide is formed by combining 116 grams of maleic acid with 432 grams of water, reacting with a reactive aluminum rod of about 54 grams, and then gradually adding 120 grams of hydrogen peroxide.

EXAMPLE 19

An aluminum oxalic peroxide is formed by combining 126 grams of oxalic acid with 432 grams of water, reacting with a reactive aluminum rod of about 54 grams, and then gradually adding 80 grams of hydrogen peroxide.

EXAMPLE 20

An aluminum benzoic peroxide is formed by combining 120 grams of benzoic acid with 146 grams of hydrogen peroxide, reacting with a reactive aluminum rod of about 54 grams. The hydrogen peroxide should be added slowly in order to control the reaction rate.

EXAMPLE 21

An aluminum stearate peroxide is formed by first dissolving 284 grams of stearic acid in 100 grams of ethyl alcohol, adding 100 grams of hydrogen peroxide, and then reacting the mixture with a reactive aluminum rod of about 108 grams. The reaction is violent and the hydrogen peroxide should be added gradually with the mixture being agitated simultaneously. The reaction should continue until a thick or viscous mass is formed.

EXAMPLE 22

An aluminum lactic peroxide is formed by reacting 106 grams of lactic acid and 381 grams of water with a reactive aluminum rod of about 54 grams and then adding about 80 grams of hydrogen peroxide.

Having thus described the invention, what I claim as new and desired to be secured by letters patent, is as follows:

1. A method of forming a peroxy compound which comprises contacting and reacting:
    a. a reactive aluminum comprising highly pure aluminum permeated with a metal having an atomic volume close to hydrogen; with
    b. a liquid mixture of
        i. hydrogen peroxide; and
        ii. a carboxylic acid; and separating the peroxy compound from unreacted reactive aluminum.

2. The method of claim 1 wherein said metal having an atomic volume close to hydrogen is selected from mercury, indium, gallium and indium/gallium alloys.

3. The method of claim 1 wherein said highly pure aluminum has a purity of at least 99.99% by weight.

4. The method of claim 1 wherein said highly pure aluminum is prepared by contacting highly pure aluminum with a metal selected from mercury, indium, gallium and indium/gallium alloys in the presence of a hydrogen ion source so as to permeate said metal through said aluminum.

5. The method of claim 1 wherein said carboxylic acid is terephthalic acid.

6. The method of claim 1 wherein said carboxylic acid is formic acid.

7. The method of claim 1 wherein said carboxylic acid is propionic acid.

8. The method of claim 1 wherein said carboxylic acid is palmitic acid.

9. The method of claim 1 wherein said carboxylic acid is butyric acid.

10. The method of claim 1 wherein said carboxylic acid is acetic acid.

11. The method of claim 1 wherein said carboxylic acid is phthalic acid.

12. The method of claim 1 wherein said carboxylic acid is caprylic acid.

13. The method of claim 1 wherein said carboxylic acid is adipic acid.

14. The method of claim 1 wherein said carboxylic acid is lauric acid.

15. The method of claim 1 wherein said carboxylic acid is acrylic acid.

16. The method of claim 1 wherein said carboxylic acid is citric acid.

17. The method of claim 1 wherein said carboxylic acid is maleic acid.

18. The method of claim 1 wherein said carboxylic acid is oxalic acid.

19. The method of claim 1 wherein said carboxylic acid is benzoic acid.

20. The method of claim 1 wherein said carboxylic acid is myristic acid.

21. The method of claim 1 wherein said carboxylic acid is tartaric acid.

22. The method of claim 1 wherein said carboxylic acid is gluconic acid.

23. The method of claim 1 wherein said carboxylic acid is stearic acid.

24. The method of claim 1 wherein said carboxylic acid is lactic acid.

25. A method of forming a peroxy compound which comprises the steps of:
   A. contacting aluminum having a purity of at least 99.99% by weight, in the presence of a hydrogen ion source, with a metal selected from mercury, indium, gallium and indium/gallium alloys to permeate said metal through said aluminum and prepare a reactive aluminum;
   B. contacting and reacting said reactive aluminum with a liquid mixture of
      i. hydrogen peroxide; and
      ii. a carboxylic acid; and
   C. separating the peroxy compound from unreacted reactive aluminum.

26. A peroxy compound prepared by contacting and reacting:
   a. a reactive aluminum comprising highly pure aluminum permeated with a metal selected from mercury, indium, gallium and indium/gallium alloys; with
   b. a liquid mixture of
      i. hydrogen peroxide; and
      ii. a carboxylic acid.

27. The peroxy compound of claim 26 wherein said highly pure aluminum has a purity of at least 99.99% by weight.

Figure 4:
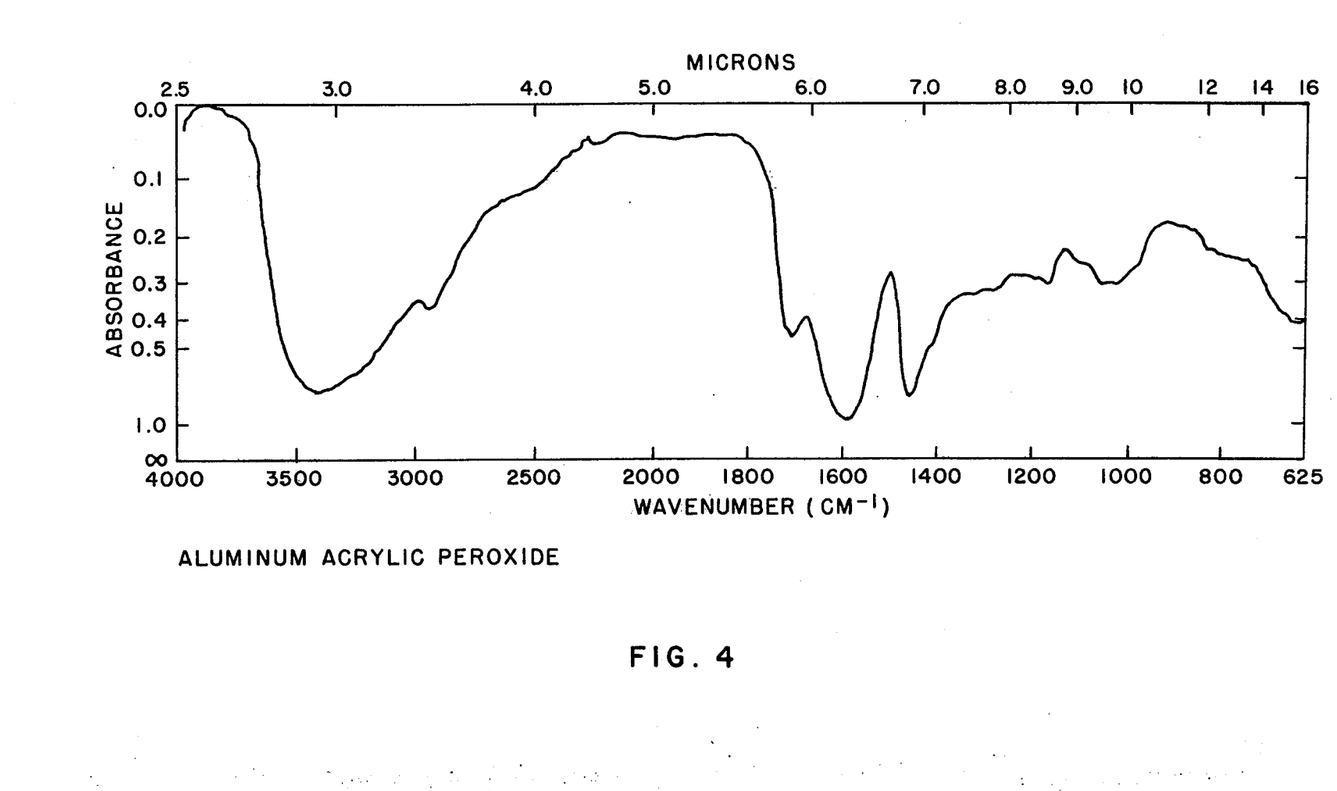

28. An aluminum acrylic peroxide having the infrared spectra as shown in FIG. 4.

Figure 3:
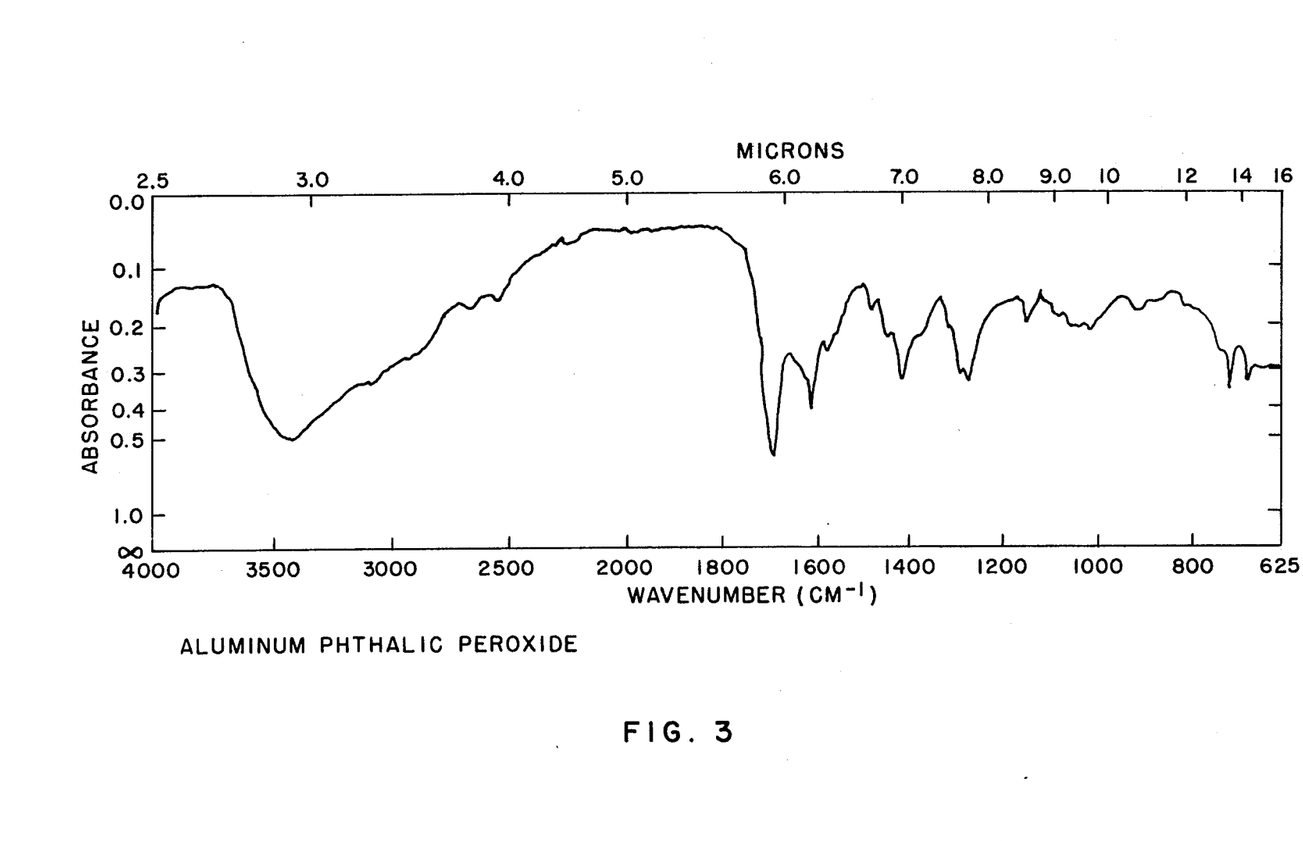

29. An aluminum phthalic peroxide having an infrared spectra as shown in FIG. 3.

Figure 2:
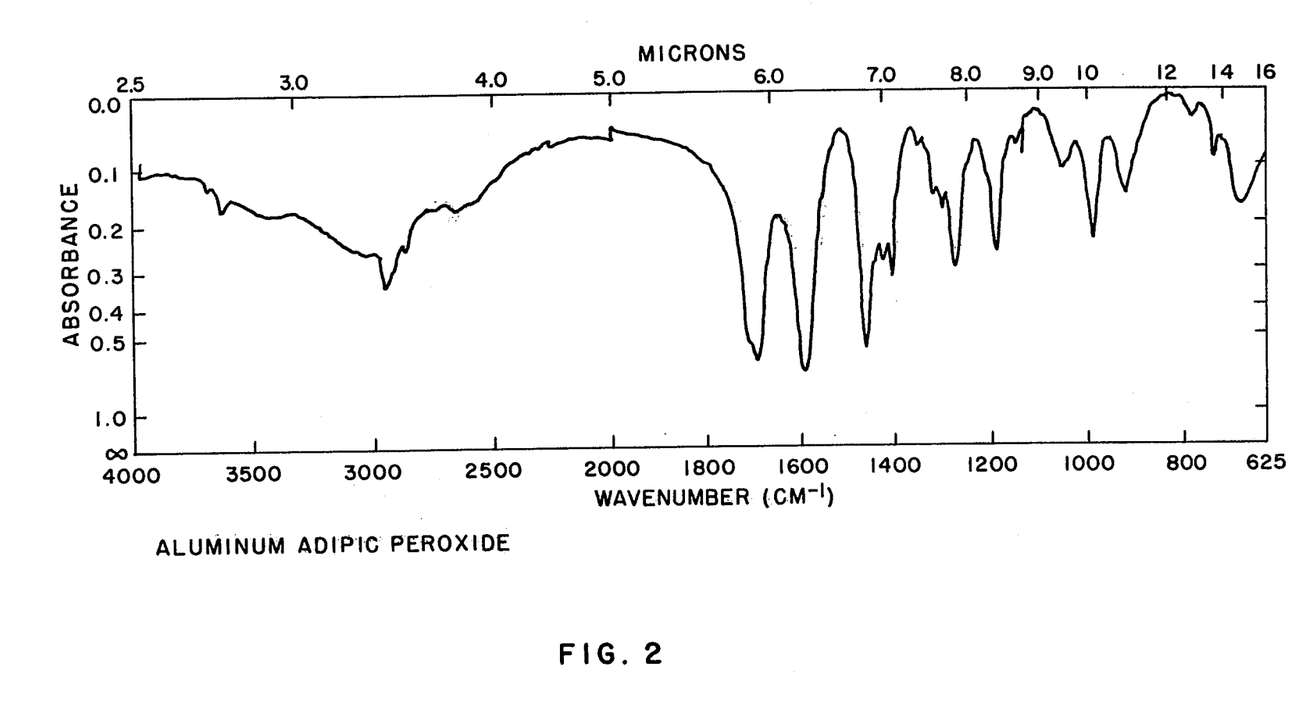

30. An aluminum adipic peroxide having an infrared spectra as shown in FIG. 2.

Figure 1:
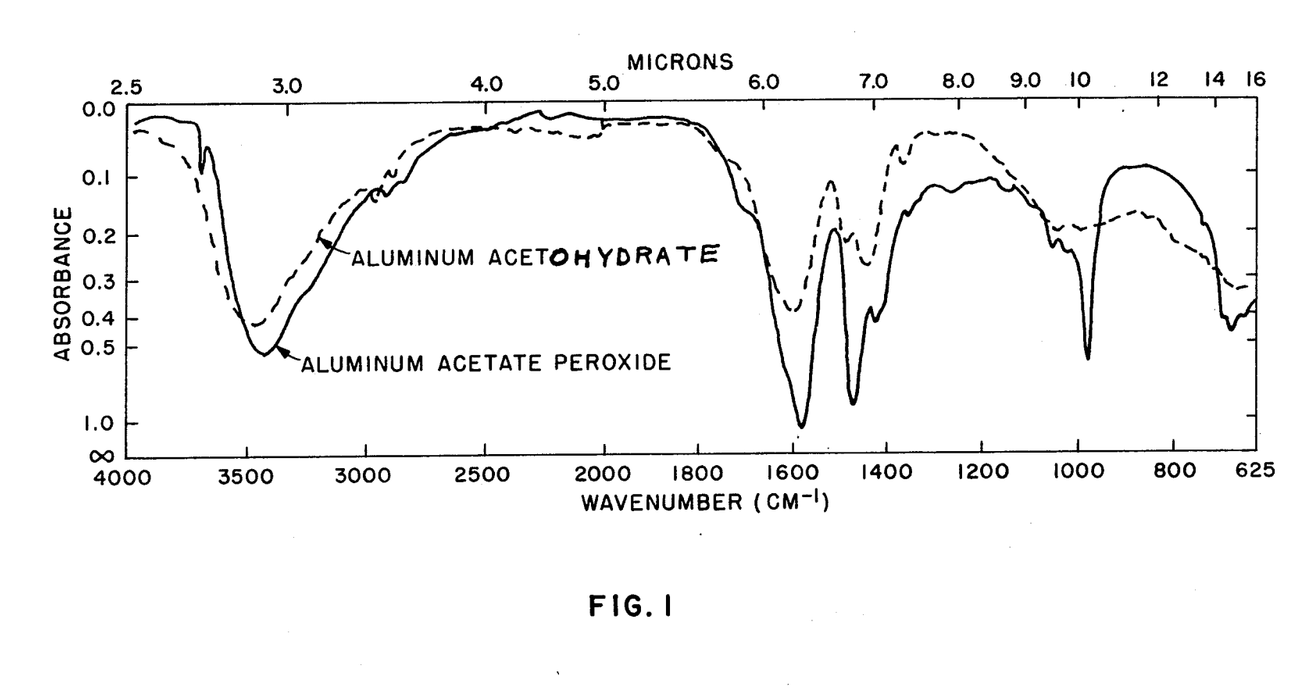
FIGS. 1 – 4 are infrared spectra responses corresponding to 4 peroxide compounds of the present invention.

31. An aluminum acetic peroxide having an infrared spectra as shown in FIG. 1.

* * * * *